(12) United States Patent
Trones et al.

(10) Patent No.: US 10,272,389 B2
(45) Date of Patent: Apr. 30, 2019

(54) DEVICES FOR ELECTROMEMBRANE EXTRACTION (EME)

(71) Applicant: Extraction Technologies Norway AS, Ski (NO)

(72) Inventors: Roger Trones, Krakstad (NO); Trond Lovli, Askim (NO); Tyge Greibrokk, Jar (NO)

(73) Assignee: EXTRACTION TECHNOLOGIES NORWAY AS, Ski (NO)

( * ) Notice: Subject to any disclaimer, the term of this patent is extended or adjusted under 35 U.S.C. 154(b) by 123 days.

(21) Appl. No.: 15/478,830

(22) Filed: Apr. 4, 2017

(65) Prior Publication Data

US 2018/0280881 A1    Oct. 4, 2018

(51) Int. Cl.

| | | |
|---|---|---|
| *B01D 61/38* | (2006.01) | |
| *B01D 61/42* | (2006.01) | |
| *B01D 15/08* | (2006.01) | |
| *G01N 30/32* | (2006.01) | |
| *G01N 30/72* | (2006.01) | |

(Continued)

(52) U.S. Cl.
CPC ........... *B01D 61/422* (2013.01); *B01D 15/08* (2013.01); *B01D 61/38* (2013.01); *B01D 61/42* (2013.01); *B01D 63/087* (2013.01); *B01L 3/5635* (2013.01); *G01N 1/4005* (2013.01); *G01N 30/32* (2013.01); *G01N 30/7233* (2013.01); *B01D 2313/13* (2013.01); *B01D 2313/345* (2013.01); *G01N 2001/4011* (2013.01); *G01N 2001/4038* (2013.01); *G01N 2030/027* (2013.01)

(58) Field of Classification Search
CPC .. B01D 61/422; B01D 15/08; G01N 30/7233; G01N 30/32; G01N 2030/027
See application file for complete search history.

(56) References Cited

U.S. PATENT DOCUMENTS

| | | | | |
|---|---|---|---|---|
| 4,006,067 A | * | 2/1977 | Gussack | .................. C23F 1/46 205/746 |
| 8,317,991 B2 | | 11/2012 | Pedersen-Bjergaard et al. | |
| 8,940,146 B2 | | 1/2015 | Trones et al. | |

FOREIGN PATENT DOCUMENTS

| | | |
|---|---|---|
| DE | 1002539 | 2/1957 |
| EP | 2461150 A2 | 6/2012 |

(Continued)

OTHER PUBLICATIONS

Huang et al.; "Development of a Flat Membrane Based Device for Electromembrane Extraction: A New Approach for Exhaustive Extraction of Basic Drugs From Human Plasma"; Journal of Chromatography A; 1326; pp. 7-12; (2014).

(Continued)

*Primary Examiner* — Arun S Phasge

(74) *Attorney, Agent, or Firm* — Cantor Colburn LLP

(57) ABSTRACT

An electromembrane extraction (EME) device including a union connector, an acceptor compartment with a connector end and a donor compartment with a connector end wherein both connector ends are connectable to the union connector, wherein the union connector includes a flat membrane with a seal on each side thereof, wherein the seals when the acceptor compartment and the donor compartment are connected to the union connector are arranged respectively between the acceptor compartment connector end and the flat membrane and the donor compartment connector end and the flat membrane.

18 Claims, 6 Drawing Sheets

(51) Int. Cl.
*B01L 3/00* (2006.01)
*B01D 63/08* (2006.01)
*G01N 1/40* (2006.01)
*G01N 30/02* (2006.01)

(56) References Cited

FOREIGN PATENT DOCUMENTS

| | | |
|---|---|---|
| WO | 0033050 A1 | 6/2000 |
| WO | 2007004892 A1 | 1/2007 |

OTHER PUBLICATIONS

Huang et al.; "Exhaustive Extraction of Peptides by Electromembrane Extraction"; Analytica Chimica Acta; 853; pp. 328-334; (2015).
Partial EP Search Report, Application No. 18162459.4-1104, dated Jul. 24, 2018; 13 pages.

* cited by examiner

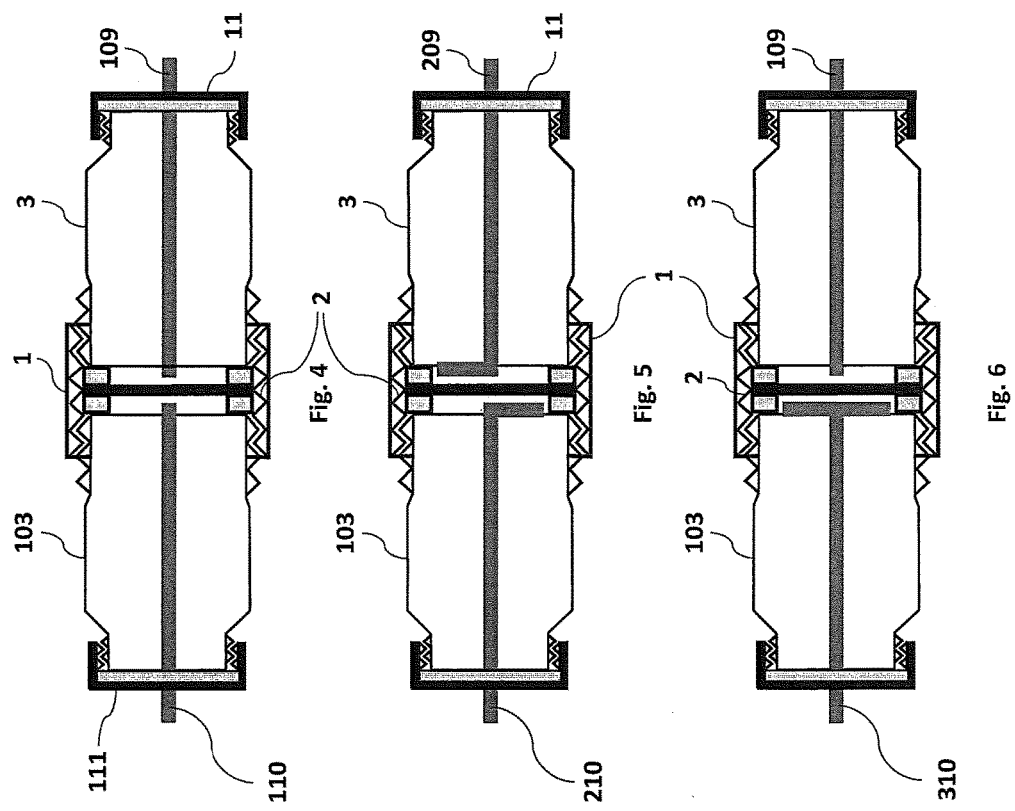

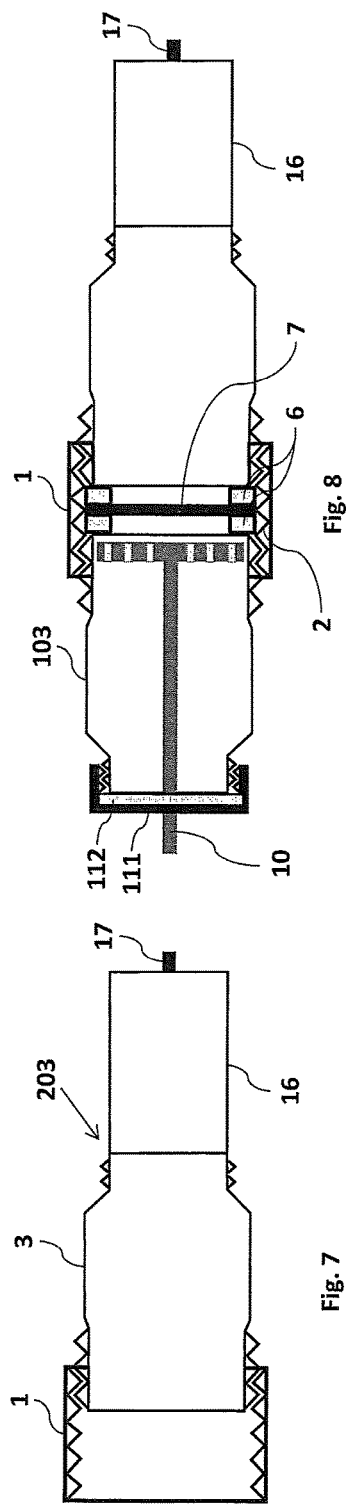
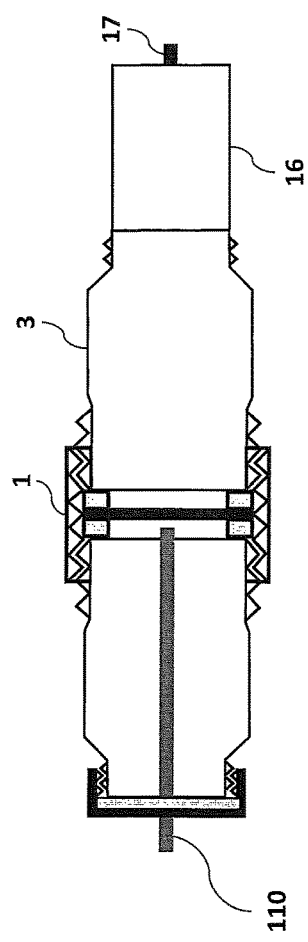
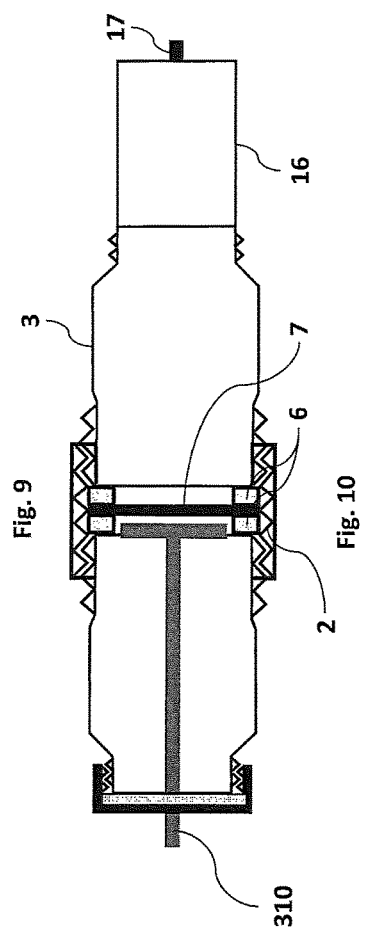

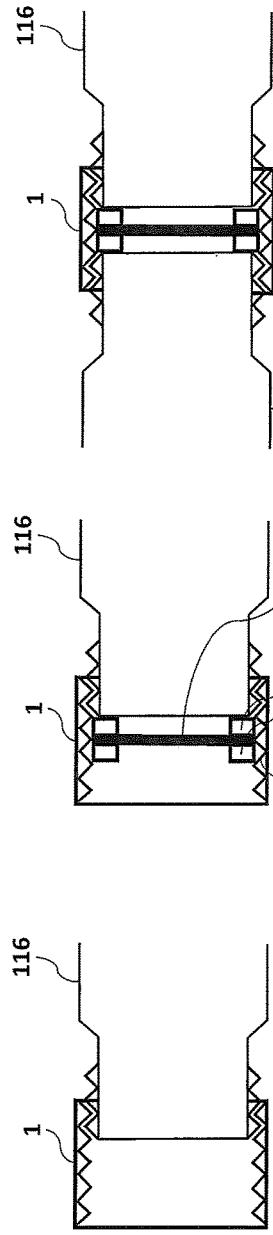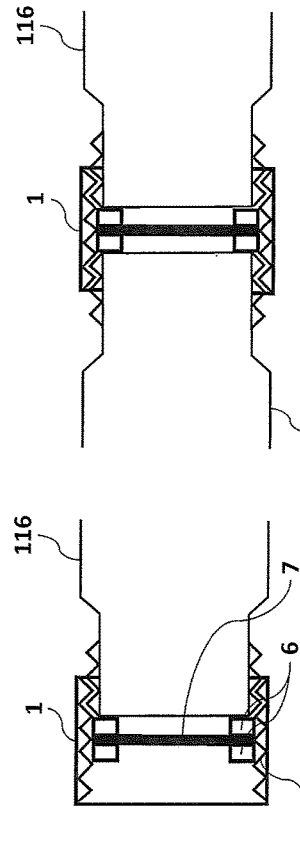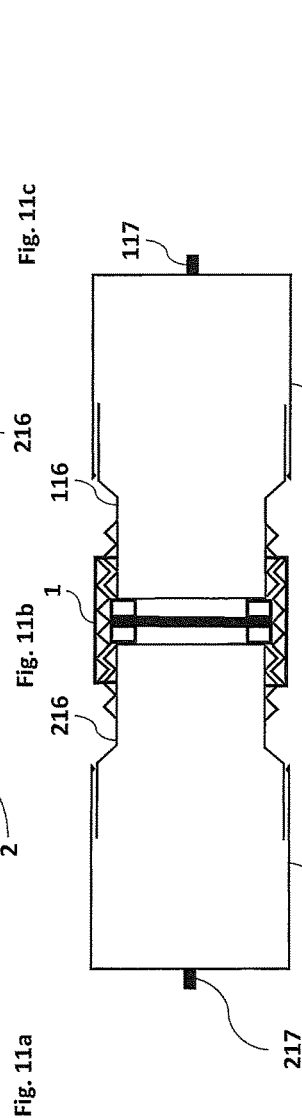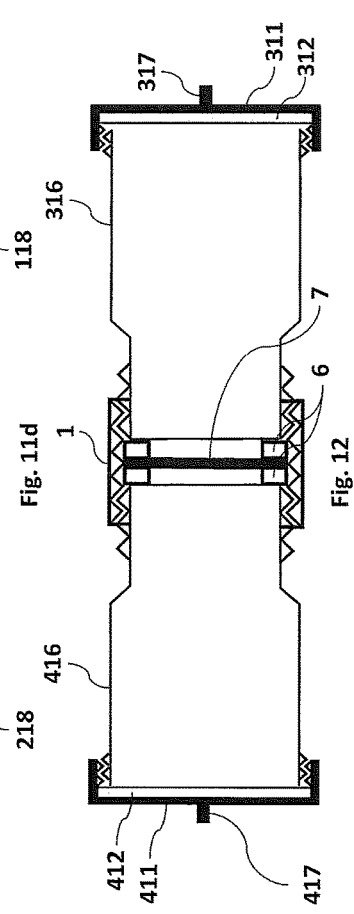

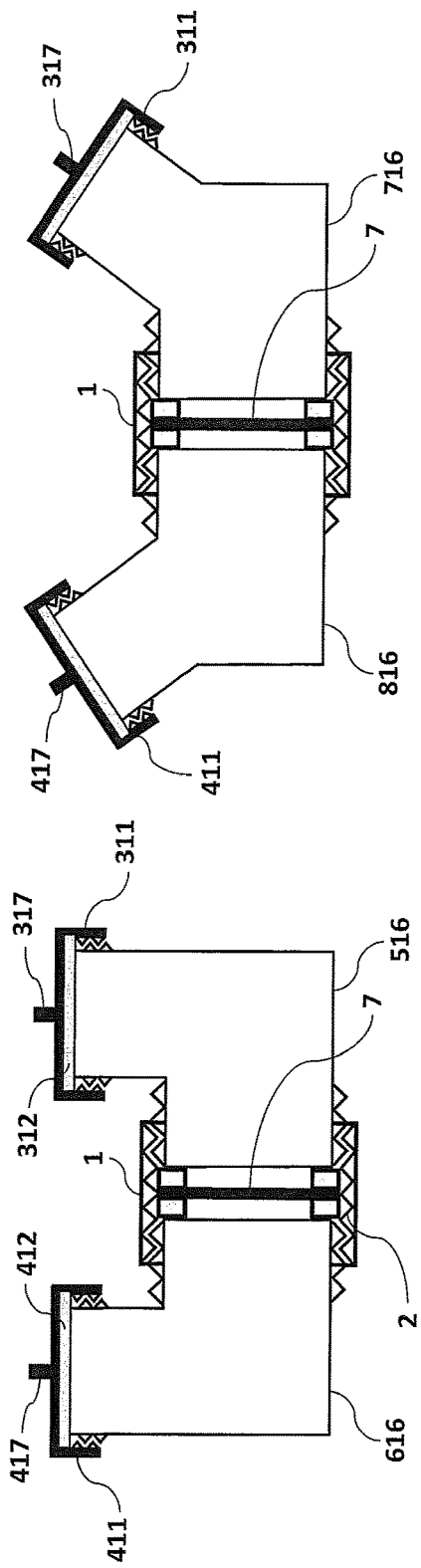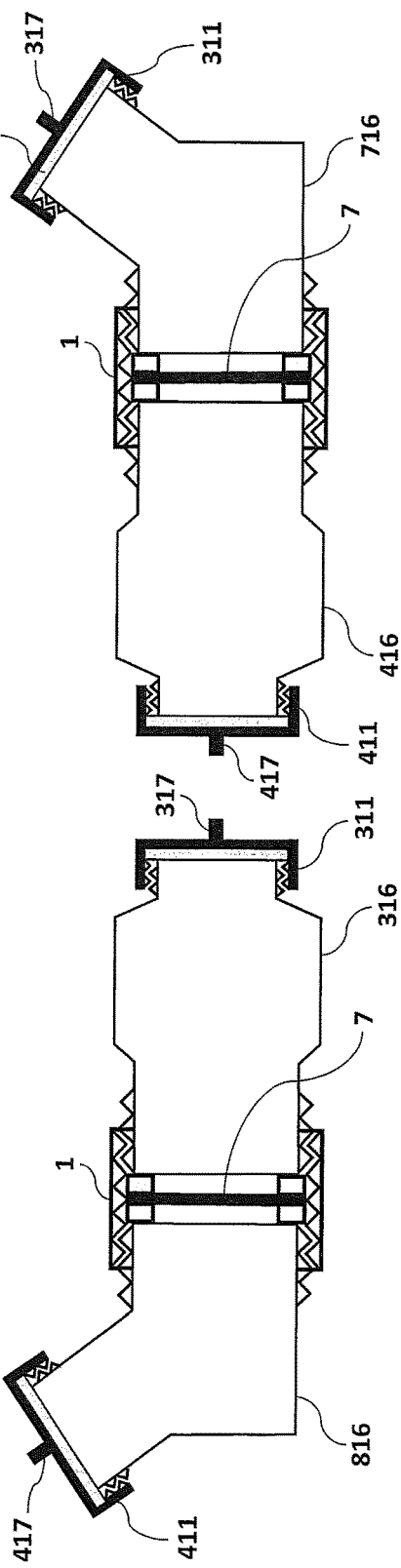

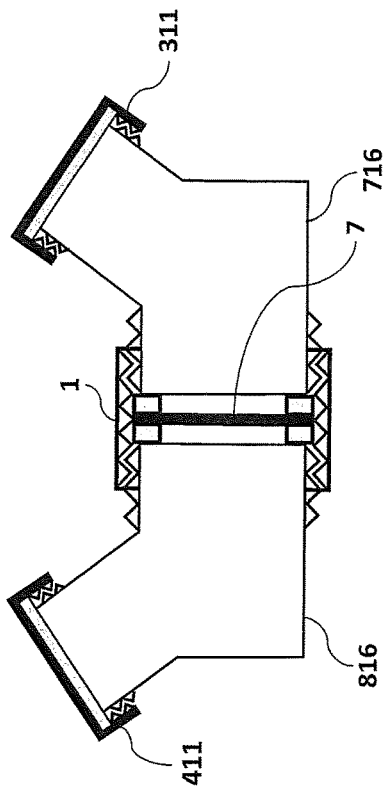
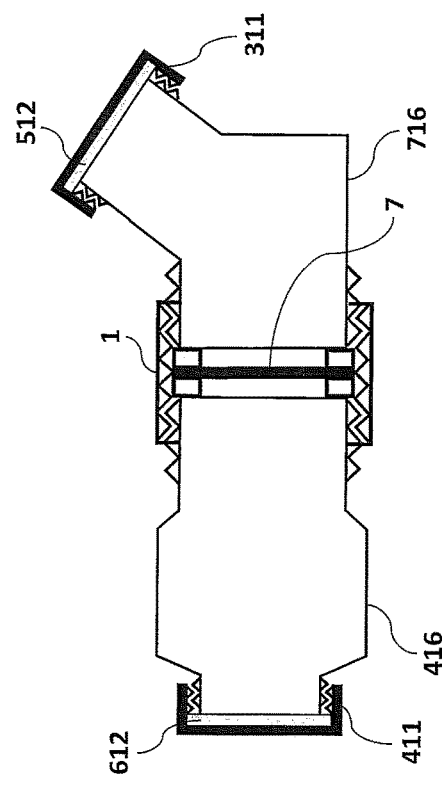
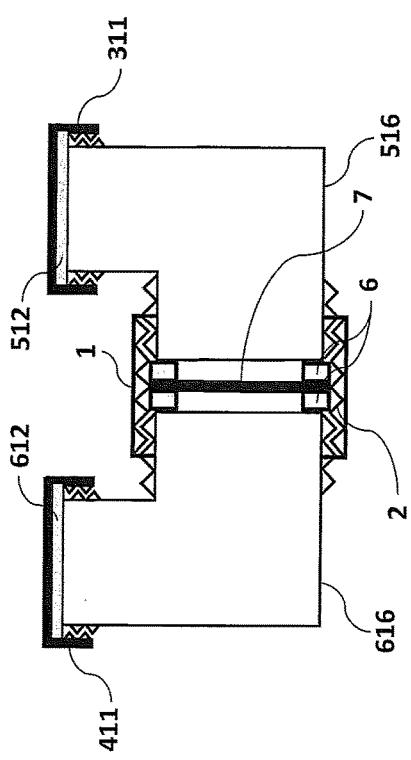
Fig. 17
Fig. 18
Fig. 19
Fig. 20

US 10,272,389 B2

DEVICES FOR ELECTROMEMBRANE EXTRACTION (EME)

FIELD OF THE DISCLOSURE

The present disclosure relates to a device for isolation, purification and/or enrichment of organic or biochemical compounds through electromembrane extraction, earlier termed as electrokinetic migration or electrokinetic cross-membrane isolation, as well as an improved processes for the use of said devices.

BACKGROUND

Analytical organic chemistry, biochemistry and medicinal chemistry are faced with a challenge of providing good methods for compounds to be detected in samples of varying origin. Often the compounds appear in complex mixtures from which they must be isolated and the compounds may also be present in very low concentrations. Another complication may be that the sample amounts containing the compounds to be detected can be very small, e.g. blood samples from infants or small children.

Many different methods for separating, isolating, purifying and concentrating bioorganic compounds have been developed over the years. Many are well-known procedures for a person skilled in the art and examples are 2-phase extraction (e.g. aqueous phase-organic phase) and 3-phase extractions (e.g. aqueous phase-organic phase-aqueous phase).

From WO0033050 there are known methods and an apparatus for 2-phase liquid and 3-phase liquid micro extraction for obtaining a high enrichment of an analyte in the acceptor solution. However, the process of classical extraction is based on diffusion of the analyte and this is a slow process. The achievable end concentration of the analyte depends on the equilibrium conditions for each of the phases in e.g. a 2- or 3-phase system, and may result in very low yields, if any.

Even though the above-mentioned processes have been automated, they are still time consuming and often also generate waste of organic solvents.

In order to improve both the selectivity as well as reducing the required time for this type of isolation procedure, the introduction of electromembrane extraction (EME) has favorably added to recent developments in this area.

It is well known that ionized chemical and biochemical substances migrate in solution under the application of an electrical field. This type of transport, which is called electrokinetic migration, is the basis for electrophoresis, and is also widely used for isolation purposes both in industrial applications (purification) and in the field of analytical chemistry (sample preparation).

Frequently, isolation based on electromembrane extraction is carried out in an aqueous one-phase system. One important example of this is electrodialysis, where ionized chemical substances are transferred from an aqueous donor/sample compartment, through the pores of an ion-exchange membrane filled with the same aqueous medium, and into an aqueous acceptor compartment. In electrodialysis, migration selectivity, which is responsible for isolation, is obtained by the presence of small pores in the polymeric membrane, preventing larger molecules from entering the acceptor compartment. Electrodialysis is an important industrial purification and desalting process, and has also been reported as a sample preparation technique in analytical chemistry.

U.S. Pat. No. 8,317,991B2 discloses a method for isolation, purification, concentration and/or enrichment of an organic or biochemical compound through electrokinetic migration i.e. electromembrane extraction (EME). A hollow fiber membrane (HFM) was stated as the most preferred device for the analytical purpose.

U.S. Pat. No. 8,940,146B2 discloses a device for electromembrane extraction, that in one embodiment of the invention utilizes a syringe needle as the second electrode (acceptor phase) together with a hollow fiber membrane.

A remaining problem to be solved with the process described in U.S. Pat. No. 8,317,991B2 is the handling and use of the device as described in said patent. As a first-generation device, there is a large potential for improvements. An improvement (as depicted in U.S. Pat. No. 8,940,146B2) simplified the whole process of electromembrane extraction, also resulting in more reliable results.

There is, however, a need for new processes giving an improved recovery of the required compounds in high purity, and last but not least, there is a need for new technology by which the isolation or purification step proceeds faster and with a high degree of automation.

A remaining challenge was how to facilitate a faster and more automated analysis of organic- or bioorganic compounds in sample solutions.

A further challenge was to improve the electrodes to provide for a faster and more automated analysis.

A further aim of the present disclosure was to provide a solution that could be combined with and used together with existing equipment.

Another aim was to provide for use of commercial automated instruments such as analytic HPLC instruments, or MS instruments such as LC-MS including automated and or robotic auto-samplers utilizing 96-well microplates.

SUMMARY

The present disclosure is directed towards handling said challenges through processes and devices as defined in the attached claims.

The present disclosure comprises replacing the hollow fiber membrane with a flat membrane, thereby providing for an incorporation in a structure applicable with a standard vial.

Thus, according to the present disclosure there is, in a first embodiment, provided for a device for electromembrane extraction (EME), comprising a snap-capped or screw-capped glass compartment for the acceptor solution, containing a custom made first disk-shaped electrode with through-holes, a threaded union connector containing the seals functioning as isolators on each side of a flat membrane and the snap-capped or screw-capped glass compartment for the donor solution containing the second custom-made disk-shaped electrode with through-holes.

In a second embodiment of the present disclosure, the donor compartment is maintained as in the first embodiment. The acceptor compartment is replaced by a custom-made compartment made from an electrically conductive resin, functioning both as an electrode and a vial, significantly enhancing the electrode surface area, with fewer mechanical components allowing for easier introduction to robotic instruments for analysis.

The novel disk-shaped electrodes with through-holes provide for a larger surface area than e.g. conventional platinum rod electrodes presently employed in EME. The through-holes are another feature to reduce the difference in ion transport distances between the back- and front side of the electrode(s) and facilitate and improve the liquid convection in the compartment(s) when in use. The disk-shaped electrode with through-holes can be made of any electrically conducting material, such as polymers, platinum, gold, silver or steel.

In a third embodiment of the present disclosure, both the donor- and acceptor compartments are custom-made from an electrically conductive resin functioning both as electrodes and vials, for even further simplification for introduction into automated/robotic systems.

The disclosure further provides for a process for electromembrane extraction (EME) of organic- or bioorganic compounds in a 3-phase system, connecting an acceptor compartment to the threaded union connector;

attaching a flat membrane in-between seals inside the threaded union connector;

including an organic liquid, preformed, manually or automatically added to the donor side of the membrane, thereby forming a supported liquid membrane (SLM) able to keep the donor and acceptor solutions apart;

providing an acceptor solution in the acceptor compartment;

adding a donor solution comprising at least one organic compound to be extracted to a donor compartment;

attaching the donor compartment to the threaded union connector, and applying electrical power (voltage) to two electrodes with 4-12 through-holes arranged in respective compartments to generate an electrical field across the SLM, or one electrode with 4-12 through-holes and one partial conductive compartment or two conductive compartments to promote the migration of said organic compound(s) from the donor solution through the SLM to the acceptor solution.

In an aspect, the process may further comprise agitating the device by vibration.

In a second aspect, the process may further comprise of no agitation of the device by vibration.

A further step of the process may include transferring the acceptor solution manually or automatically by e.g. an autosampler for analysis in a dedicated analytical instrument.

The disclosure includes a process for preparing a sample for analysis (or isolation), comprising the steps of, providing a first hydrophilic donor solution comprising at least one organic compound to be transferred from said donor solution to an acceptor solution;

the pH of said donor solution being at a level where said organic compound is either positively or negatively ionized, if necessary, by adjusting the pH;

providing a second hydrophilic acceptor solution;

the pH of said second hydrophilic acceptor solution being at a level wherein said compound to be transferred from the donor solution to the acceptor solution, is ionized, if necessary by adjusting the pH;

providing a supported liquid membrane whose thickness is in the range of 10-1000 µm comprising an immobilized organic liquid, which is substantially immiscible with water, which an electrical field and said at least one ionized organic compound can traverse; and placing said membrane in fluid contact with said donor solution and said acceptor solution, so that it separates said donor solution and said acceptor solution;

providing electrodes and/or electrically conductive compartments to be placed in fluid contact with the donor solution and with the acceptor solution;

applying a voltage across said electrodes and/or conductive compartments to promote the migration of said organic compound from the donor solution through the supported liquid membrane to the acceptor solution; and detecting said organic compound by a suitable detector system and/or checking for biological activity in a biological test system.

Also included is a process for purification of a sample, comprising the steps of providing a first hydrophilic donor solution comprising at least one organic compound to be transferred from said donor solution to an acceptor solution; the pH of said donor solution being at a level where said organic compound is either positively or negatively ionized, if necessary, by adjusting the pH;

providing a second hydrophilic acceptor solution;

the pH of said acceptor solution being at a level wherein said compound to be transferred from the donor solution to the acceptor solution is ionized, if necessary, by adjusting the pH;

providing a supported liquid membrane whose thickness is in the range of 10-1000 µm, comprising an immobilized organic liquid, which is substantially immiscible with water, which an electrical field and said at least one ionized organic compound can traverse; and placing said membrane in fluid contact with said donor solution and said acceptor solution, so that it separates said donor solution and said acceptor solution;

providing electrodes and/or conductive compartments to be placed in fluid contact with the donor solution and with the acceptor solution; and applying voltage across said electrodes and/or conductive compartments to promote the migration of said organic compound from the donor solution through the supported liquid membrane to the acceptor solution; optionally isolating said at least one organic compound through removal of the acceptor solution, if necessary, after adjusting the pH of the solution.

The present disclosure can be adapted to use with an autosampler that may involve using e.g. conductive 96-well microplates adapted to transfer electrical current to an electrode/conductive vial arranged therein.

The present disclosure provides for use of EME in commercial automated instruments such as analytic HPLC instruments, or MS instruments such as LC-MS instruments. The obtained acceptor solution is transferred to a dedicated analytical instrument such as analytic HPLC instruments, or MS instruments such as LC-MS or including automated and or robotic auto-samplers utilizing 96-well microplates for further analysis.

BRIEF DESCRIPTION OF THE FIGURES

FIG. 4: Illustrates the cross-sectional view of EME equipment with closed vials and installed syringe needle electrodes.

FIG. 5: Illustrates the cross-sectional view of EME equipment with closed vials and installed L-shaped syringe electrodes.

FIG. 6: Illustrates the cross-sectional view of EME equipment with closed vials and an installed T-shaped syringe electrode and a syringe needle electrode.

FIG. 7: Illustrates the cross-sectional view of a threaded union connector connected to an acceptor vial including a conductive vial part.

FIG. 8: Illustrates the cross-sectional view of EME equipment with closed vials and installed electrode, including a vial according to FIG. 7.

FIG. 9: Illustrates the cross-sectional view of EME equipment with closed vials and an installed syringe needle electrode, including a vial according to FIG. 7.

FIG. 10: Illustrates the cross-sectional view of EME equipment with closed vials and installed T-shaped syringe electrode, including a vial according to FIG. 7.

FIG. 11a: Illustrates the cross-sectional view of a threaded union connector connected to a part of a conductive acceptor vial.

FIG. 11b: Illustrates the cross-sectional view of a threaded union connector with a flat membrane installed in-between seals therein connected to a part of a conductive acceptor vial.

FIG. 11c: Illustrates the cross-sectional view of a threaded union connector connected to a part of a conductive acceptor vial and a part of a conductive donor vial with a flat membrane installed.

FIG. 11d: Illustrates the cross-sectional view of EME equipment with closed conductive vials.

FIG. 12: Illustrates the cross-sectional view of EME equipment with conductive vials closed by conductive caps.

FIG. 13: Illustrates the cross-sectional view of EME equipment with conductive angled vials closed by conductive caps.

FIG. 14: Illustrates the cross-sectional view of EME equipment with conductive angled vials closed by conductive caps.

FIG. 15: Illustrates the cross-sectional view of EME equipment with conductive vials, with an angled donor vial closed by conductive caps.

FIG. 16: Illustrates the cross-sectional view of EME equipment with conductive vials, with an angled acceptor vial closed by conductive caps.

FIG. 17: Illustrates the cross-sectional view of EME equipment with conductive angled vials closed by conductive caps with conductive septa.

FIG. 18: Illustrates the cross-sectional view of EME equipment with conductive angled vials closed by conductive caps with conductive septa.

FIG. 19: Illustrates the cross-sectional view of EME equipment with conductive vials, with an angled donor vial closed by conductive caps with conductive septa.

FIG. 20: Illustrates the cross-sectional view of EME equipment with conductive vials, with an angled acceptor vial closed by conductive caps with conductive septa.

DETAILED DESCRIPTION

Figure 3:
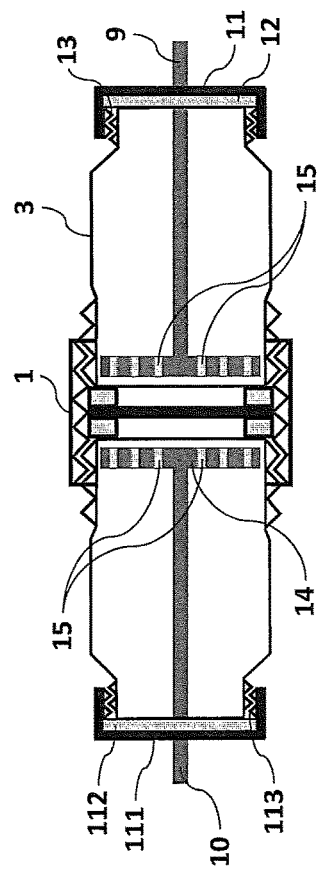
FIG. 3: Illustrates the cross-sectional view of EME equipment with closed vials and installed electrodes.

A first embodiment is depicted herein (FIGS. 1-6). A second embodiment (FIGS. 7-10), containing the acceptor compartment made from an electrically conductive resin, functioning both as an electrode and vial. A third embodiment (FIGS. 11-20), containing both the donor and acceptor compartments made from an electrically conductive resin both functioning as electrodes and vials, with the purpose of automated analyses with robotic systems. All embodiments (1-3) resulted in extractions with good to excellent yields of examples of bioorganic compounds from donor solutions. A special electrode used in embodiments 1 and 2 is shown in FIGS. 3 and 8. The devices contained in the present disclosure were designed with the intention to utilize the present devices or modified devices in commercial automated instruments such as e.g. analytical HPLC instruments, or MS instruments such as LC-MS.

The present disclosure will now be explained in further detail with reference to the Figures that illustrates a number of different embodiments of an electromembrane extraction (EME) device.

Figure 1D:
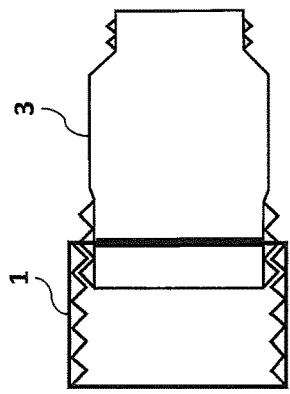
FIG. 1d: Illustrates the cross-sectional view of a threaded union connector with a flat membrane installed in-between seals.
Figure 1C:
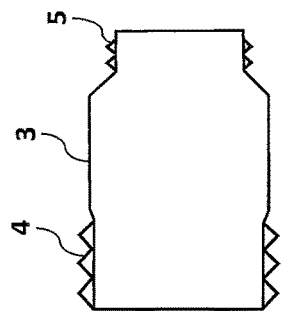
FIG. 1c: Illustrates the cross-sectional view of a threaded union connector connected to an acceptor vial.
Figure 1B:
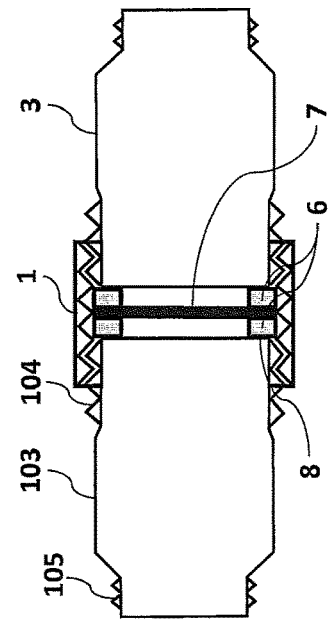
FIG. 1b: Illustrates the cross-sectional view of an acceptor vial.
Figure 1A:
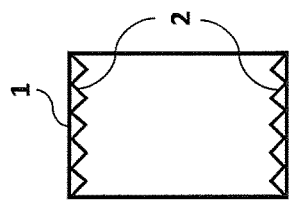
FIG. 1a: Illustrates the cross-sectional view of a threaded union connector.

FIG. 1a shows a union connector 1 provided with internal threads 2. The union connector 1 is shaped like an open tube. The union connection is preferably made of an electrically insulating material. FIG. 1b illustrates an acceptor vial/compartment 3 comprising external threads 4 at a connector end and external cap connection element 5 at a cap end. In one embodiment, the cap connection element 5 is threads adapted to connect with a screw cap with internal threads. Alternatively, the cap connection element is an external flange adapted to connect with a snap cap. The acceptor vial 3 is in this embodiment initially open in both ends. In FIG. 1c, the acceptor vial 3 and the union connector 1 have been connected through the threads 2 and 4. In FIG. 1d, Teflon seals 6 and a flat membrane 7 have been arranged within the union connector 1. The seals 6 are preferably ring shaped and can be made of Teflon or similar materials. The flat membrane 7 spans the cross section of the opening of the tube-shaped union connector 1 and one seal is arranged between the connector end of the acceptor vial and the flat membrane providing a sealed connection 8 there between. The seal 6 also supports the flat membrane and keeps it in place within the union connector 1.

Figure 2:
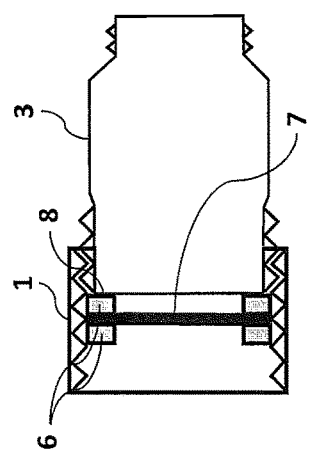
FIG. 2: Illustrates the cross-sectional view of a threaded union connector with acceptor and donor vial arranged opposite the membrane.

In FIG. 2, a donor vial/compartment 103 has been connected to the union connector 1 on the opposite side through external threads 104 on a connector end therefor. The donor vial 103 is in this embodiment identical to the acceptor vial and open in both ends. Cap connector elements 105 are arranged on the cap end opposite the connector end for connection of a cap with threads or a snap cap. A sealing connection 8 has been established between the connector end of the donor vial 103 and the seal 6. In use, the flat membrane is a supported liquid membrane (SLM). Prior to and during the initial part of the assembly, the flat membrane 7 may only be a support structure to be wetted with an organic liquid to form a SLM. First after arrangement in the union connector and possibly after connection of one or both of the compartments is the organic liquid supplied to the membrane from the donor side of the membrane to form the SLM.

FIG. 3 illustrates the system of FIG. 2 after installation of electrodes 9 and 10 on respectively the acceptor and the donor side of the flat membrane. The illustrated electrodes comprise a rod with a disk-shaped element 14 to be arranged at a given distance from the membrane. Each of the disks 14 comprises a number of through-holes 15 improving the possibility for an acceptor solution and a donor solution to circulate in the area of the disk 14. The rods of the electrodes 9 and 10 extend through septa 12, 112 and caps 11 and 111 respectively for connection to a power supply. The caps are arranged to contain the acceptor and donor solutions in their respective vials.

FIG. 4 illustrates a similar embodiment as FIG. 3 but with syringe needle electrodes 109, 110 penetrating the respective caps with septa.

FIG. 5 illustrates a similar embodiment as FIG. 4 but with L-shaped syringe electrodes 209, 210 penetrating the respective caps with septa.

FIG. 6 illustrates a similar embodiment as FIG. 4 but with a T-shaped syringe donor electrode 310. Although only illustrated as a donor electrode also the acceptor electrode can be T-shaped. A person skilled in the art will appreciate that the different electrodes can be freely combined.

FIG. 7 shows a union connector 1 assembled with a custom made partial conductive acceptor vial 203 consisting of a glass vial 3 and a conductive vial 16 included a conductive plug 17 for connection to a power supply. The partial conductive vial 203 is functioning both as an electrode and a vial.

FIG. 8 illustrates the system of FIG. 7 with a donor vial 103 assembled in a union connector 1 with internal threads 2, a flat membrane 7 assembled in-between Teflon seals 6 included a disk-shaped donor electrode with through-holes 10. The electrode 10 perforates donor septum 112 and extends through donor cap 111, respectively for connection to a power supply.

FIG. 9 illustrates a similar embodiment as FIG. 8 but with a syringe needle electrode 110.

FIG. 10 illustrates a similar embodiment as FIG. 8 but with a T-shaped syringe donor electrode 310.

FIG. 11a shows a union connector 1 assembled with a connection section of a conductive acceptor vial 116.

FIG. 11b illustrates the system of 11a with a flat membrane 7 assembled in-between Teflon seals 6 arranged within the union connector 1 with internal threads 2.

FIG. 11c illustrates the system of FIG. 11b with a connection section of a conductive donor vial 216 arranged within the union connector 1.

FIG. 11d illustrates the system of FIG. 11c assembled with a conductive acceptor vial 118 containing a conductive acceptor plug 117 and a conductive donor vial 218 containing a conductive donor plug 217.

FIG. 12 shows a union connector 1 assembled with a flat membrane 7 in-between Teflon seals 6, a conductive acceptor vial 316 containing a conductive acceptor cap 311, an acceptor septum 312 and a conductive acceptor cap plug 317. Further, a conductive donor vial 416 assembled within the union connector 1, containing a conductive donor cap 411, a donor septum 412 and a conductive donor cap plug 417.

FIG. 13 illustrates the system of FIG. 12 assembled with a conductive angled acceptor vial 516 and a conductive angled donor vial 616.

FIG. 14 illustrates the system of FIG. 12 assembled with a conductive angled acceptor vial 716 and a conductive angled donor vial 816.

FIG. 15 illustrates the system of FIG. 12 assembled with a conductive acceptor vial 316 and a conductive angled donor vial 816.

FIG. 16 illustrates the system of FIG. 12 assembled with a conductive angled acceptor vial 716 and a conductive donor vial 816.

FIG. 17 shows a union connector 1 with internal threads 2 assembled with a flat membrane 7 in-between Teflon seals 6, a conductive angled acceptor vial 516 with a conductive acceptor cap 311 containing a conductive acceptor septum 512. Further, a conductive angled donor vial 616 assembled within the union connector 1 with a conductive donor cap 411 containing a conductive donor septum 612.

FIG. 18 illustrates the system of FIG. 17 assembled with a conductive angled acceptor vial 716 and a conductive angled donor vial 816.

FIG. 19 illustrates the system of FIG. 17 assembled with a conductive acceptor vial 316 and a conductive angled donor vial 816.

FIG. 20 illustrates the system of FIG. 17 assembled with a conductive angled acceptor vial 716 and a conductive donor vial 416.

Embodiment 1; containing a snap-capped glass compartment with treads for the donor solution, and a custom made first disk-shaped electrode with through-holes, a threaded union connector containing the Teflon seals functioning as isolators on each side of the flat membrane and the snap-capped glass compartment with treads for the acceptor solution containing the second custom-made disk-shaped electrode.

Embodiment 2; containing a donor compartment maintained as in the first embodiment (with a single electrode), a threaded union connector containing the Teflon seals functioning as isolators on each side of the flat membrane and the acceptor compartment replaced by a custom-made compartment made from an electrically conductive material such as a conductive resin or metal, functioning both as an electrode and a vial.

Embodiment 3; containing custom made donor- and acceptor compartments made from an electrically conductive material. Connected by a threaded union connector containing the Teflon seals functioning as isolators on each side of the flat membrane. The donor- and acceptor compartment is functioning both as electrodes and vials.

The Figures illustrate different embodiments of the present invention. A person skilled in the art will appreciate that one embodiment of an element illustrated in one Figure may be exchanged with another embodiment of the element illustrated in another Figure within the scope of the present invention.

Electromembrane Extraction (EME)

The equipment used for electromembrane extraction (EME) is illustrated in FIGS. 3-6, 8-10 and 11d-20. The DC power supply utilized was e.g. the model ES 0300-0.45 from Delta Elektronika BV (Zierikzee, Netherlands) with a programmable voltage in the range of 0 to 300V, providing current in the range of 0 to 450 mA. (A pulsed DC power supply may also be utilized). A standard 9V battery was employed for a DC voltage of 9V, as well as e.g. wiring 9V batteries in series to a required voltage between e.g. 9V to 200V. Two disk-shaped electrodes with through-holes according to FIG. 3 were utilized in examples of the first embodiment while a partial electrically conductive compartment together with a single disk-shaped electrode with through-holes according to FIG. 8 were utilized in the examples of the second embodiment. Two electrically conductive compartments according to FIG. 11d were utilized in the examples of the third embodiment. The electrode(s) and the electrically conductive compartment(s) were all connected to a power supply, when in operation. Glass or electrically conductive donor and acceptor compartments with a volume of 100-5000 µL was connected to a threaded union connector containing Teflon seals functioning as isolators on each side of the flat membrane. The 3-20 mm i.d. flat membrane was immobilized with an organic liquid to a supported liquid membrane (SLM). To the acceptor compartment was added 100-5000 µL of an aqueous solution, and the compartment was equipped with a snap cap or a threaded cap. To the donor compartment was added 100-5000 µL of a donor solution, and the compartment was equipped with a snap cap or a threaded cap to provide an operational device. The membrane could e.g. be Accurel® PP 1E (R/P), Accurel® PP 2E HF (R/P) polypropylene membranes (Membrana, Wuppertal, Germany) or any membrane prepared to function as a supported liquid membrane. The PP 1E membrane had a diameter of 8 mm, a thickness of about 110 μm, and a pore size of 0.1 μm. The PP 2E had a diameter of 8 mm, a thickness of about 168 μm, and a pore size of 0.2 μm. Both disk-shaped electrodes with through-holes in embodiment 1 and the single disk-shaped electrode with through-holes in embodiment 2 were made of steel and adjusted to a distance of 2-5 mm from the membrane prior to connecting the electrodes to a power supply. The sample could be "agitated" by a vibration unit as e.g. IKA MS3 digital (IKA-Werke GmbH & Co. KG, Germany) at 0-1500 rpm and a voltage of 0-300V applied for 1-45 minutes.

EME was performed according to the following procedure; Donor and acceptor compartments with a volume of 100-5000 μL were connected to a threaded union connector containing Teflon™ seals functioning as isolators on each side of the flat membrane. The flat membrane was immobilized to a supported liquid membrane with 3-30 μL of an organic liquid typically 2-nitrophenyl octyl ether (NPOE), 1-ethyl-2-nitrobenzene (ENB), 2,4-dimethyl-1-nitrobenzene (DNB), 1-isopropyl nitrobenzene (INB), 1-heptanol, 1-octanol, 1-nonanol, 1-decanol, 1-undecanol, bis(2-ethylhexyl) phosphate (BEHP), bis(2-ethylhexyl) phosphite (BEHPi) or mixtures thereof, or another organic liquid for pre-immobilization manually or automatically of a flat membrane to a supported liquid membrane. The acceptor compartment was added 100-5000 μL of an aqueous solution, typically 10 mM HCl, 20 mM HCOOH, 20 mM CH$_3$COOH, 20 mM CF$_3$COOH or a phosphate buffer. The donor compartment was added 100-5000 μL of a donor solution and equipped with a snap cap or a threaded cap to obtain an EME device ready for operation.

In the second embodiment, the donor compartment was maintained as in the first embodiment (with a single electrode), a threaded union connector containing the Teflon seals functioning as isolators was placed on each side of the flat membrane and the acceptor compartment was replaced by a custom-made compartment made from an electrically conductive resin, functioning both as an electrode ad a vial.

In the third embodiment, custom made donor- and acceptor compartments made from an electrically conductive resin were utilized. The compartments were connected by a threaded union connector containing the Teflon seals functioning as isolators on each side of the flat membrane. The donor- and acceptor compartment function both as electrodes and vials.

Finally, the vibration unit was turned on ad voltage (0-300V) was applied for e.g. 25 minutes. After electromembrane extraction, the acceptor solution was collected and subsequently transferred for further analysis in a dedicated analytical instrument either manually or automatically.

Without being held to theory, the inventors consider the following to be the theoretical basis of the present disclosure: In order to enable EME, the whole system comprising the donor solution, the supported liquid membrane (SLM), and the acceptor solution should serve as an electrical circuit. The main electrical resistance of the system is related to the supported liquid membrane (and its composition) which is critical in ensuring penetration of the electrical energy. Thus, the polarity of the organic liquid immobilized in the flat membrane should have a sufficient polarity to ensure a sufficient electrical conductance to secure penetration of the electrical field. Essentially, the cross-membrane transport of model analytes increased with decreasing electrical resistance of the supported liquid membrane. However, provided that the supported liquid membrane and the model analytes are inert to electrode reactions, electrolysis may occur in the donor and acceptor solutions as a result of increased conductivity:

Donor solution: $H_2O \rightarrow 2H^+ + \frac{1}{2}O_2 + 2e^-$

Acceptor solution: $2H^+ + 2e^- \rightarrow H_2$

Electrolysis may lead to bubble formation (of oxygen and hydrogen), causing pH changes, i.e. a decreased pH in the acceptor solution (with a cathode, negative electrode) and an increased pH in the donor solution (with an anode, positive electrode). Both cases may seriously affect extraction recoveries, robustness and repeatability.

Electrolysis is known to be of little impact in electromembrane extraction (EME) if the generated system-current is less than 50 μA (<50 μA). Formation of electric double layers is another complication known to reduce the efficiency and stability of an electrokinetic process. An increased electrode surface, as partly maximized in the second embodiment and fully maximized in the third embodiment, is expected to reduce the formation of electric double layers, thereby stabilizing the system-current at a low level. An increased electrode surface is also expected to allow lower voltages without reducing the recoveries. For safety reasons, lower voltages, such as e.g. 100V (concurrent with a system-current below 20 μA) or below, are preferred, both for manually operated devices as well as for automated dedicated robotic instruments.

For embodiment 1 the system-current was below 50 μA and for embodiment 2 and 3 below 20 μA (typically between 10-20 μA).

Basic Analytes

In the donor solution, pH will be adjusted into the acidic range to ensure that the basic model analytes (B) are totally protonated (BH+). After applying an electrical potential difference across the SLM, the protonated model analytes will start their electrokinetic migration from the donor solution towards the negative electrode placed in the acceptor solution (or the negatively charged conductive compartment). In the aqueous donor solution, the electrical field strength (V/cm) will be relatively low due to the low electrical resistance of this phase. Because the model analytes are totally protonated they will migrate rapidly towards the supported liquid membrane. These rapid migrations will also be promoted by using a donor compartment which ensures a short migration distance to the supported liquid membrane. The different model analytes will migrate with different velocity in the donor solution based on their charge to-size ratio, but that is expected only to be a minor factor responsible for the differences observed in their individual transport efficiencies (recovery values).

Secondly, the model analytes will cross the interface to the supported liquid membrane. In this phase, the electrical field strength (V/cm) will be high due to the high electrical resistance of the organic liquid used. Consequently, their electrokinetic migration will be strongly suppressed in this medium because deprotonation of the basic substances will (probably) occur in the non-polar medium. In other words, the migration inside the supported liquid membrane, (is believed) to be strongly controlled by the following equilibrium: $\rightarrow BH^+ B + H^+$ For compounds with a low degree of deprotonation, the electromembrane extraction through the supported liquid membrane will be relatively high, whereas strongly deprotonating compounds will show a very low electromembrane extraction and will effectively be discriminated by the supported liquid membrane. Without being held to theory, this is expected to be the principal reason for the differences in the extraction recoveries that is observed. In addition, differences in the charge-to-size ratios will also be expected to affect the individual transport efficiencies in the supported liquid membrane.

If electrolysis becomes a major problem, a modification/optimization of the SLM may be needed in addition to utilize a buffer or a higher concentration of the acid in the acceptor compartment.

Acidic Analytes

The new devices (embodiment 1-3) and methods of the present disclosure may be applied to any organic compounds capable of being partly or completely ionized. Thus, for acidic drugs, alkaline (or neutral) conditions in the donor and acceptor solutions are preferred. For acidic analytes (anionic species), the direction of the electrical field is reversed (compared to EME of basic analytes). The cathode (negative electrode) is located in the donor compartment while the anode (positive electrode) is located in the acceptor compartment.

The donor- and acceptor solutions will e.g. be made alkaline to approximately pH 12 with e.g., NaOH or a buffer, to promote negatively charged analytes. The organic liquid (e.g. n-octanol) is immobilized on the donor side of the flat membrane. The acceptor compartment is added an alkaline aqueous acceptor solution, e.g. 10 mM NaOH or a buffer. The donor compartment is added an alkaline aqueous donor solution e.g. 10 mM NaOH or a buffer.

By use of embodiment 1, the two electrodes are adjusted to their optimized positions relative to the flat membrane.

By use of embodiment 2, the single electrode (in the donor compartment) is adjusted to its optimized position relative to the flat membrane.

By use of embodiment 3 there is no need for adjusting electrodes because the compartments are electrically conductive i.e. they function both as electrodes and vials. The vibration unit could be activated at 0-1500 rpm and, finally, the electrodes will be connected to a power supply and e.g. 0-300V will typically be applied for e.g. 1-45 minutes.

EXAMPLES

Example 1: Initial Experiments

The basic experiments will be performed on new devices for electromembrane extraction (EME) as illustrated in FIGS. 3-6, 8-10 and 11d-20. A threaded union connector containing the Teflon™ seals functioning as isolators on each side of the flat membrane is connected with the acceptor- and donor compartments, respectively. The addition of an organic liquid from the donor side of the flat membrane follows, typically 10 μL of 2-nitrophenyl octyl ether (NPOE) (for basic analytes) or 1-octanol (for acidic analytes) to immobilize the organic liquid in the pores of the flat membrane to a supported liquid membrane (SLM), or by a liquid phase made by synthetic reactions, or by synthetic modification of the membrane surface. The acceptor compartment will be added the acceptor solution and closed by a threaded cap or a snap cap. The donor solution, acidified with HCl (approximately pH 2) to ionize basic analytes of interest or made alkaline with NaOH (approximately pH 12) to ionize acidic analytes of interest will be added to the donor compartment and closed by a threaded cap or a snap cap prior to EME. The device will then be placed in a "device holder". The electrodes will be connected to a power supply and [e.g., up to] 300V will typically be applied for 1-45 minutes. Finally, the vibration unit and then the power supply will be turned on. After electromembrane extraction (EME), the vibration unit and the power source will be turned off and the acceptor solution will be collected and subsequently transferred for further analysis in a dedicated analytical instrument.

Three different drugs will be selected as model analytes to test the new EME devices, namely: Quetiapine, methadone and sertraline, at concentrations of 5 μg/mL down to 0.15 μg/mL (therapeutic concentrations) in 10 mM HCl or from human blood samples diluted in 20 mM HCl spiked with the analytes in quest.

Example 2: Exemplary EME Protocol

The main equipment used for the extraction (EME) procedures is shown in FIGS. 3-6, 8-10 and 11d-20, in addition to a power supply with a programmable voltage in the range of 0-300V with a current output in the range of 0-450 mA. The EME device (first embodiment) was agitated at 1000 rpm on e.g. a IKA MS3 digital with an adjustable agitation speed in the range of 0-1500 rpm. The polypropylene flat membranes utilized were Accurel® PP 1E (R/P), Accurel® PP 2E HF (R/P) from Membrana (Wuppertal, Germany) with an outer diameter (OD) of 8 mm, a thickness of 110-168 μm and a pore size of 0.1-0.2 μm, respectively.

The following analytes were selected as model analytes for testing of the first embodiment (with two disk-shaped electrodes with through-holes);

quetiapine, a mixture of methadone and sertraline and a mixture of quetiapine, methadone and sertraline. The donor solutions were made up to a total of 1500 μL of the analytes in 10 mM HCl, with a concentration ranging from 0.84 μg/mL to 5 μg/mL.

EME was performed according to the following procedure; a threaded union connector containing the Teflon seals functioning as isolators on each side of the flat membrane was connected with the acceptor- and donor compartments, respectively. The flat membrane was immobilized from the donor side of the flat membrane by NPOE, to a supported liquid membrane (SLM). To the acceptor compartment was added 600 μL of 10 mM aqueous HCl, and the compartment was closed by a threaded cap or a snap cap and to the donor compartment was added 600 μl of an acidified donor solution and the compartment was closed by a threaded cap or snap cap. Both electrodes were adjusted to their optimized positions relative to the flat membrane. The EME device was then placed on the IKA vibrator and connected to the power supply. Finally, the vibration unit and power supply was turned on at, respectively, 1000 RPM and 300V for 25 minutes. After electromembrane extraction, the acceptor solution was transferred for further analysis in a dedicated analytical instrument.

In the first embodiment, utilizing Accurel® PP 1E membranes, several consecutive experiments gave the following average recovery of the analytes from 0.84 μg/mL to 5 μg/mL standard solutions;

Quetiapine: 9% to 40%
Methadone: 71% to 81%
Sertraline: 63% to 78%

With the Accurel® PP 2E membranes several consecutive experiments gave the following average recovery of the analytes from 0.84 μg/mL to 5 μg/mL standard solutions;

Quetiapine: 20% to 60%
Methadone: 78% to 84%
Sertraline: 73% to 81%

During the electromembrane extraction, the system-current increased somewhat, typically up to about 50 μA, and a varying system-current output, demonstrating a process which is not in complete equilibrium. This is also well known from former work with electromembrane extraction. An increasing system-current above a certain level (about 50 μA) would leave the extraction process prone to electrolysis.

In the second embodiment (with a single disk-shaped steel electrode with through-holes), when the electrically conductive compartment was initially installed as the donor compartment, the recoveries never exceeded 20%. However, when the electrically conductive resin compartment was installed as the acceptor compartment, first examined with quetiapine as analyte in 1.25 μg/mL to 5 μg/mL concentrations (with PP 2E membranes, 300V and 25 minutes at 1000 rpm), the recovery increased to 74-86%. The volumes of the donor and the acceptor compartments were varied from 600 μL to 2000 μL.

The recoveries were then examined with a mixture of methadone and sertraline at lower voltages, with the electrically conductive resin as acceptor compartment;

|  | 9 V | 50 V | 150 V |
| --- | --- | --- | --- |
| Methadone: | 79% | 76% | 74% |
| Sertraline: | 10% | 70% | 67% |

During the electromembrane extraction, the system-current increased slightly, typically up to about 20 μA with a stable system-current output indicating a stable process in equilibrium.

In the third embodiment (with two electrically conductive compartments functioning both as vials and electrodes) with a volume of 700 μL each and the usage of the Accurel® PP 2E membranes the recoveries at 9V, 50V and 100V were measured to;

|  | 9 V | 50 V | 150 V |
| --- | --- | --- | --- |
| Methadone: | 85-88% | 92% | 88-89% |
| Sertraline: | 25-29% | 85% | 83-86% |

During the electromembrane extraction, the system-current increased slightly, typically to between 10-20 μA with a very stable system-current output, indicating a process in equilibrium.

Samples of human plasma diluted and acidified with 20 mM HCl to approximately pH 2, spiked with methadone and sertraline at 0.15 μg/mL (therapeutic dose), with NPOE immobilized in the flat membrane to a supported liquid membrane (SLM) gave recoveries of 60% of methadone and 81% of sertraline at 100V. The recoveries at 50V and 200V were similar but slightly lower at 200V.

Samples of human plasma diluted and acidified with 20 mM HCl to approximately pH 2, spiked with quetiapine to a concentration of 0.15 μg/mL (therapeutic dose), resulted in an average recovery (with an organic liquid made up of 30% bis(2-ethylhexyl) phosphite (BEHPi) in NPOE (v/v) immobilized in the flat membrane to a supported liquid membrane (SLM) of 43% at 100V, increasing to 56% at 250V.

Both embodiment 2 and embodiment 3 showed a surprising stability towards system-current build-up that could hamper the extraction process caused by electrolysis and thereby reduce the recovery significantly. In all experiments (non-optimized), utilizing these embodiments the generated system-current was below 20 μA (typically between 10-20 μA) for spiked acidified water samples.

The same embodiments were highly stable in contact with spiked human plasma samples. The generated system-current was below 20 μA in all experiments, even with e.g. pure NPOE as organic liquid or a combination of e.g. NPOE and BEHPi to be immobilized in the flat membrane to make the supported liquid membrane (SLM).

With basis in the low system-current generated, the chosen organic liquids or the combination thereof immobilized in a flat membrane, to make a SLM, apparently discriminated mass transfer of background electrolyte ions and matrix ions from human plasma. If not, the system-current would be far higher because of an increased flow of ions, increasing the conductance across the flat membrane and thereby causing electrolysis to be the predominant process reducing the recovery.

| Reference numbers | |
| --- | --- |
| 1 | Threaded union connector |
| 2 | Internal threads |
| 3 | Acceptor vial |
| 4 | Acceptor vial connector end external threads |
| 5 | Acceptor vial cap end external threads |
| 6 | Teflon seal |
| 7 | Flat membrane |
| 8 | Sealing contact |
| 9 | Disk-shaped acceptor electrode with through-holes |
| 10 | Disk-shaped donor electrode with through-holes |
| 11 | Acceptor cap |
| 12 | Acceptor septum |
| 13 | Acceptor cap internal threads |
| 14 | Electrode disk |
| 15 | Through-hole |
| 16 | Conductive vial |
| 17 | Conductive plug |
| 103 | Donor vial |
| 104 | Donor vial connector end external threads |
| 105 | Donor vial cap end external threads |
| 109 | Syringe needle acceptor electrod |
| 110 | Syringe needle donor electrode |
| 111 | Donor cap |
| 112 | Donor septum |
| 113 | Donor cap internal threads |
| 116 | Connection section of a conductive acceptor vial |
| 117 | Conductive acceptor plug |
| 118 | Conductive acceptor vial |
| 203 | Partial conductive acceptor vial |
| 209 | L-shaped syringe acceptor electrode |
| 210 | L-shaped syringe donor electrode |
| 216 | Connection section of a conductive donor vial |
| 217 | Conductive donor plug |
| 218 | Conductive donor vial |
| 310 | T-shaped syringe donor electrode |
| 311 | Conductive acceptor cap |
| 312 | Acceptor septum |
| 316 | Conductive acceptor vial |
| 317 | Conductive acceptor cap plug |
| 411 | Conductive donor cap |
| 412 | Donor septum |
| 416 | Conductive donor vial |
| 417 | Conductive donor cap plug |
| 512 | Conductive acceptor septum |
| 516 | Conductive angled acceptor vial |
| 612 | Conductive donor septum |
| 616 | Conductive angled donor vial |
| 716 | Conductive angled acceptor vial |
| 816 | Conductive angled donor vial |

The invention claimed is:

1. An electromembrane extraction (EME) device comprising
a union connector,
an acceptor compartment with an acceptor compartment connector end, and
a donor compartment with a donor compartment connector end,
wherein both the acceptor and donor compartment connector ends are connectable to the union connector,
wherein the union connector is made of electric insulating material,
wherein the union connector comprises a flat membrane with a seal on each side thereof, wherein the seals when the acceptor compartment and the donor compartment are connected to the union connector are arranged respectively between the acceptor compartment connector end and the flat membrane and the donor compartment connector end and the flat membrane.

2. The EME device according to claim 1, wherein at least one of the acceptor compartment and the donor compartment comprises an opening closed with a cap.

3. The EME device according to claim 2, wherein the acceptor compartment and or the donor compartment comprising the opening closed with a cap has an angled configuration providing for the opening to be arranged at a level above the membrane.

4. The EME device according to claim 2, wherein the cap is a threaded cap or a snap cap.

5. The EME device according to claim 2, wherein the cap comprises a septum, wherein the septum is arranged to be penetrated by a syringe needle electrode(s), or a L-shaped- or a T-shaped syringe electrode(s) or a disk-shaped electrode(s) with through-holes.

6. The EME device according to claim 5, wherein the septum is made of conductive material.

7. The EME device according to claim 1, wherein the seals are ring shaped, support the flat membrane and are made of electric insulating material.

8. The EME device according to claim 1, wherein a part of the acceptor compartment and or the donor compartment is made of a conductive material.

9. The EME device according to claim 8, wherein the acceptor compartment and or the donor compartment comprises a conductive plug for transferring electric current to the compartment(s) comprising the plug(s).

10. The EME device according to claim 1, wherein the acceptor compartment and or the donor compartment is made of a conductive material.

11. The EME device according to claim 10, wherein the acceptor compartment and or the donor compartment comprises a conductive plug for transferring electric current to the compartment(s) comprising the plug(s).

12. The EME device according to claim 1, wherein the acceptor compartment and or the donor compartment is made of glass.

13. A process for electromembrane extraction (EME) of an organic compound in a 3-phase system, comprising
connecting a union connector to a connector end of an acceptor compartment, wherein the union connector comprises a flat membrane with a seal on each side thereof, and wherein the flat membrane and one of the seals seal off the connector end of the acceptor compartment, wherein the flat membrane comprises a supported liquid membrane;
connecting a connector end of a donor compartment to the union connector opposite the acceptor compartment, wherein the flat membrane and one of the seals seal off the connector end of the donor compartment;
providing an acceptor solution in the acceptor compartment;
arranging an acceptor electrode in the acceptor compartment;
closing the acceptor compartment with a cap with threads or a snap cap arranged at a cap end opposite the connector end;
providing a donor solution comprising at least one organic compound to be extracted in the donor compartment;
arranging a donor electrode in the donor compartment;
closing the donor compartment with a cap with threads or a snap cap arranged at the cap end opposite the connector end; and
applying electrical power to the acceptor- and donor electrodes to promote the migration of said organic compound from the donor solution through the supported liquid membrane to the acceptor solution.

14. The process according to claim 13, further comprising agitating the donor- and acceptor solutions by vibration.

15. The process according to claim 13, wherein the acceptor solution is transferred to a dedicated analytical instrument such as analytic HPLC instruments, or MS instruments such as LC-MS or including automated and or robotic autosamplers utilizing 96-well microplates for further analysis.

16. The process according to claim 13, wherein the supported liquid membrane to be selected is based on the polarity of said at least one organic compound.

17. The process according to claim 16, wherein the artificial liquid membrane is 2-nitrophenyl octyl ether (NPOE) for hydrophobic compounds.

18. The process according to claim 16, wherein the artificial liquid membrane is 10-50% bis(2-ethylhexyl) phosphite in NPOE for more hydrophilic compounds.

* * * * *